United States Patent [19]

Anderson

[11] Patent Number: 5,660,830
[45] Date of Patent: Aug. 26, 1997

[54] SOLUBILIZING COUNTER-IRRITANTS AND CONCURRENTLY EXTRACTING CAPSAICIN FROM THE SAME SPECIFIC PEPPERS

[76] Inventor: Cleve Richard Anderson, 85-175 Farrington Hwy. A432, Makaha, Hi. 96792

[21] Appl. No.: 305,668

[22] Filed: Sep. 14, 1994

[51] Int. Cl.⁶ .......................... A61K 35/78; A61K 31/16
[52] U.S. Cl. .................. 424/195.1; 514/627; 514/825; 514/906
[58] Field of Search .................. 424/195.1; 514/627, 514/825, 906

[56] References Cited

U.S. PATENT DOCUMENTS

| | | | |
|---|---|---|---|
| 4,012,505 | 3/1977 | Boici | 424/195.1 |
| 4,592,912 | 6/1986 | Nickolaus | 424/195.1 |
| 5,178,879 | 1/1993 | Adekunle et al. | 424/484 |
| 5,296,225 | 3/1994 | Adekunle et al. | 424/195.1 |

*Primary Examiner*—John W. Rollins

[57] ABSTRACT

Counter-irritants produce a slight irritation, as on an area of the skin, in order to relieve more serious inflammation elsewhere. Peppers, members of the Capsicum species, are a source of counter-irritants. The Scoville rating for a pepper provides a measure of the counter-irritant content of a given pepper. This invention provides for the solubilizing and recovery of the counter-irritants contained within peppers, having Scoville ratings of from 30,000 to 250,000, in the common capsaicin containing ethyl alcohol extract from the same specific peppers. The synergisitic pain relieving benefits of the counter-irritants in combination with the capsaicin provides superior pain relief for many hours after an application.

3 Claims, No Drawings

SOLUBILIZING COUNTER-IRRITANTS AND CONCURRENTLY EXTRACTING CAPSAICIN FROM THE SAME SPECIFIC PEPPERS

FIELD OF THE INVENTION

The subject invention produces a topical analgesic product combining the counter-irritants solubilized from peppers, a member of the Capsicum species, with the capsaicin concurrently extracted from those same peppers.

SUMMARY OF THE INVENTION

This invention provides for the solubilizing and recovery of the counter-irritants contained within peppers having Scoville ratings from 30,000 to 250,000 in the common capsaicin containing ethyl alcohol extract from the same specific peppers. The unique process uses 190 proof ethyl alcohol containing five percent isopropyl alcohol to solubilze the counter-irritants. Either pure ethyl alcohol or ethyl alcohol as low as 140 proof may also be used. The process can be conducted on either a batch or continuous basis. The batch method was used in these studies; at the same time, it is recognized that a continuous process could have certain cost advantages and require different time and temperature parameters.

Equal quantities of chopped peppers and ethyl alcohol are placed in a closed container and maintained at a room temperature of 70° to 75° fahrenheit. Most of the capsaicin content of the pepper is extracted into the ethyl alcohol within the first few hours. For several days the pepper pulp remains cohesive and difficult to stir. On or about the eighth day a significant change occurs. The pepper mass becomes readily fluidized as the counter-irritants contained in the peppers solubilize. Concurrently the liquid changes from a light green over to finally a deep green color. The resulting deep green product provides superior synergistic pain relief from the solubilized counter-irritants in combination with the extracted capsaicin.

ALTERNATIVE ANALGESICS

Extensive field testing of the subject analgesic with its synergistic pain relief benefits of the counter-irritants in combination with the extracted capsaicin has established that it is superior to currently available OTC products for relief of muscle strain and osteoarthritic-type pain. The potential market is large. According to the Arthritis Foundation report, Wall Street Journal, Sep. 7, 1989, over thirty-six million Americans are afflicted with osteoarthritis. Many more are believed to suffer from muscle strain.

Capsaicin is readily soluble in the 190 proof ethyl alcohol used in the process; much of the capsaicin contained within the pepper is extracted within the first few hours. Essentially all the contained capsaicin is in solution by the eighth day of this process. The capsaicin content of the extract from the various peppers that may be utilized in this process range from 0.2percent (0.3%) for an extract from a pepper having a Scoville rating of 30,000 up to 1.67 percent (2.0%) for a pepper such as the Habanero pepper from Central America which has a Scoville rating of 250,000.

The Scoville rating is a measure of the capsaicin content of peppers. Dividing the Scoville rating of a pepper by fifteen (15) gives the parts per million (ppm) capsaicin content of that specific pepper.

Capsaicin is believed to ease pain by blocking pain messages carried to the brain by C-fiber nerves associated with hot and cold sensations. Capsaicin is the active ingredient in several OTC medicated creams. The advertised capsaicin content of these OTC products ranges from 0.025 percent up to 0.075 percent capsaicin.

The capsaicin used in current OTC analgesics is a commercial product that has been recovered from peppers such as the Asian Hot pepper. It is expensive, costing as much as $230.00 per gram in pure crystal form. The 60 percent pure commercial grade of capsaicin when purchased in 20 to 40 kilogram quanitites still costs $14.00 per gram of contained capsaicin. For capsaicin containing OTC creams, this is a major cost factor. The cost for the capsaicin alone in the 0.075 percent capsaicin product can add over fifty percent to ingredient costs for producing these current OTC capsaicin containing analgesics. This high cost for the capsaicin added to these existing OTC analgesics would impose a severe cost penalty for increases in their capsaicin content much above the 0.075 percent level.

By contrast, in the subject invention the capsaicin in combination with the counter-irritants is recovered in situ in a cost effective single step process. The analgesic product produced by the subject invention can contain from 0.30 percent up to 2.0 percent capsaicin at costs competitive with current OTC analgesics containing only 0.075 percent capsaicin. At the minimum concentration of 0.30 percent the subject product contains four-fold the capsaicin content of current topical analgesics available in the OTC market. At the higher capsaicin content of 2.0 percent, the subject product contains over twenty-five times the capsaicin content of current OTC topical analgesics available in the OTC market.

The high concentration of capsaicin in the subject product is important by itself for relieving pain. The synergistic pain relieving properties of the counter-irritants in combination with the contained capsaicin provides superior pain relief that is sustained for many hours.

The Physicians Desk Reference for nonprescription drugs, 1988 Edition, reports that many available topical OTC analgesic formulations contain some form of, or derivative of, salicylate as their prime pain relief agent. The heat-like reaction they produce usually persists for only an hour or two.

Aspirin, or its derivatives, is a primary drug for oral use. However, where one or two aspirin tablets often prove effective in lessening headache pain, it is common to require ten to twelve or more aspirin-type tablets per day, taken orally, to provide significant relief from osteoarthritic-type pain. Steady dosage is essential to keep inflammation under control. Many patients, up to fifty percent or more, find that they suffer from internal bleeding and gastrointestinal upsets from such high dosages. Buffered, enteric-coated, or nonacetylated aspirin are commonly used to temper the gastrointestinal side effects from taking plain aspirin.

Acetaminophen is the best known OTC oral analgesic for relieving the pain of arthritis. It, though, possesses no anti-inflammatory properties. Trade name products include Tylenol, Datril and Panadol.

Ibuprofen is a very popular drug of the nonsteroidal anti-inflammatory type. Trade name products include Advil, Nuprin, Motrin, and Rufen.

Propoxy is a common narcotic analgesic used to control arthritic-type pain. A trade name product is Darvon.

Codeine is another popular analgesic for treating severe arthritic-type pain. The trade name product, Tylenol, contains codeine with numbers after Tylenol referring to the concentration. Tylenol #1 has no codeine, #2 has 15 mg., #3 has 30 mg., #4 has 60 mg. Codeine can be habit forming and it should not be used with alcohol.

Corticosteroids or cortisones are available in many forms including injection into the afflicted joint(s). There can be serious side effects from the use of cortisone with the body's ability to make cortisone hormones being suppressed after longterm use. These hormones produced by the body's adrenal gland are important in dealing with stress and infection. Professional medical supervision is critical for patients using cortisone.

THE PROCESS

Peppers having a Scoville rating of 30,000 or more are used in the process with the Serrano being the pepper of immediate choice because of its ready commercial availability. The peppers are harvested while still brilliant green in color, firm to the touch, and sized at about one hundred peppers per pound. These freshly harvested Serrano peppers are shipped in "cooler" trailer trucks direct from the producers to the extraction facility.

A batch-type extraction process has been used although it is recognized that the process can be adapted to continuous processing. Such a continuous process could have differing time, temperature and concentration parameters than those of the batch process.

The pepper is diced into pieces approximately one-quarter inch in girth and length. The subsequent process proceeds uniformly and predictably with this size of pepper particle. Larger pieces slow the extraction process. Dicing to smaller sizes results in production of a fine pepper "flour" which impedes both the extraction and filtering process.

The alcohol is 190 proof ethyl alcohol containing five percent isopropyl denaturant. Sixty-four ounces of diced peppers are transferred to covered polypropylene leaching containers and sixty-four ounces of the 190 proof alcohol is added which fills the voids among the diced peppers and, in addition, provides a liquid cover of about one-half inch.

The batch-type process is carried out at a room temperature of 70° to 75° F. Within the first few hours, a light green color develops in the liquid.

The extraction process continues until there is a marked change in the physical nature and color of the batch. Up to about the eighth day, the Serrano pepper pulp remains cohesive. On or about the eighth day, in the matter of a few hours, a significant change occurs. The pulp mass, which had been cohesive and difficult to stir, becomes more free moving. By the tenth day, the pulp mass is easily fluidized. As the cohesiveness of the mass decreases with the solubilizing of the counter-irritants, the extract changes from a light green over to a deep green color.

The pain relieving properties of the extract increases markedly as the counter-irritants contained in the pepper solubilize. The extract product with its combined counter-irritants and capsaicin content provides superior pain relief for many hours. The extract product is separated from the pepper residue by filtering through a fine non-gauze filter. The product retains its superior pain relieving qualities over an extended storage period of several months.

The starting peppers must be handled with care. Their counter-irritant content is highly irritating to the skin and workers must wear protective clothing including gloves. Essentially all the counter-irritants contained in the starting peppers is solubilized into the capsaicin containing alcohol extract. Only a trace of counter-irritants remains in the residual pepper pulp which can be handled with bare hands, if desired, without discomfort.

I claim:

1. A process for the preparation and recovery of the counter-irritants and capsaicin contained in Capsicum sp., said counter-irritants having a Scoville rating of from 30,000 to 250,000, said process comprises:
    a. mixing a batch of diced peppers in an equal quantity by weight of 190 proof ethyl alcohol in a covered container,
    b. steeping the mixture at 70 to 75 F, for eight to ten days to extract the capsaicin and counter-irritants, the extract is characterized by the extractant liquid changing color.
    c. separating the extractant from the residue by filtration.

2. The process of claim 1 wherein the extract contains capsaicin ranging from about 0.20 percent up to about 1.67 percent by weight of the extract.

3. The topical analgesic extract product comprising the counter-irritants prepared by the process according to claim 1 or claim 2.

* * * * *